United States Patent [19]

Koga et al.

[11] Patent Number: 5,352,450
[45] Date of Patent: Oct. 4, 1994

[54] METHOD FOR PREPARING VACCINE FOR DENTAL CARIES AND VACCINAL COMPOSITIONS FOR DENTAL CARIES USED AS NASAL DROP

[75] Inventors: Toshihiko Koga, Tokyo; Nobuo Okahashi, Komae; Ichiro Takahashi, Yokohama; Koji Shibuya; Hirotaka Ohta, both of Kanagawa, all of Japan

[73] Assignees: Lion Corporation; National Institute of Health, both of Tokyo, Japan

[21] Appl. No.: 529,602

[22] Filed: May 29, 1990

[30] Foreign Application Priority Data

May 29, 1989 [JP] Japan .................. 1-137025
Aug. 9, 1989 [JP] Japan .................. 1-207700

[51] Int. Cl.⁵ .............. A61K 39/02; A61K 39/00; C12P 21/06; C12P 21/04
[52] U.S. Cl. .............. 424/190.1; 424/242.1; 424/244.1; 435/69.1; 435/71.2; 435/252.3; 530/350
[58] Field of Search .............. 435/69.1, 71.2, 172, 435/252.3; 424/92, 88, 93 H; 530/350

[56] References Cited

U.S. PATENT DOCUMENTS

| | | | |
|---|---|---|---|
| 4,442,085 | 4/1984 | Colman et al. | 424/49 |
| 4,448,768 | 5/1984 | Colman et al. | 424/92 |
| 4,521,513 | 6/1985 | Russell | 435/68 |
| 4,693,888 | 9/1987 | Miyahara et al. | 424/49 |
| 4,725,428 | 2/1988 | Miyahara et al. | 424/50 |

FOREIGN PATENT DOCUMENTS

| | | |
|---|---|---|
| 49062624 | 10/1972 | Japan . |
| 55-069516 | 5/1980 | Japan . |
| 56-501364 | 4/1981 | Japan . |
| 57-114526 | 7/1982 | Japan . |
| 58-500948 | 6/1983 | Japan . |
| 58-164518 | 9/1983 | Japan . |
| 60-064930 | 4/1985 | Japan . |
| 62-215534 | 9/1987 | Japan . |
| 2060647 | 5/1981 | United Kingdom .......... C07G 7/00 |

OTHER PUBLICATIONS

Lehner et al., Inf & Immun. 34:407-415, "Immunization with Purified Protein Antigens from *Streptococcus mutans* against Dental Caries in Rhesus Monkeys" 1981.
Ohta et al., The Journal of Gen. Microbiology. 135:981-988 1989, "Characterization of a cell-surface protein antigen of hydrophilic *Streptococcus mutans* strain GS-5".
Old et al. Principles of Gene Manipulation p. 4 Blackwell 1980.
Sommer J. of Bact 169:5167-5173 (1987).
Holt et al. Inf & Imm 38:147-156 1982.

(List continued on next page.)

*Primary Examiner*—Christine M. Nucker
*Assistant Examiner*—Hazel F. Sidberry
*Attorney, Agent, or Firm*—Burns, Doane, Swecker & Mathis

[57] ABSTRACT

A method for preparing a vaccine for dental caries comprises the step of culturing a variant which is obtained by integrating a protein antigen (PAc)-expressing gene into the chromosomal gene of a *Streptococcus mutans* GS-5 strain to obtain the protein antigen, the protein antigen being produced on the surface of cells of oral *Streptococcus mutans* or it being extracellularly produced by the microorganism and having a molecular weight ranging from about 170,000 to 220,000. *Streptococcus mutans* GS-5 (K-3), in which a protein antigen-expressing gene is integrated into the chromosomal gene thereof, has an ability of producing the protein antigen on the surface of the cells or extracellularly. A preventive vaccine composition for dental caries for nasal drops comprises the protein antigen thus produced by the strain: *Streptcoccus mutans*, the vaccine being intranasally administered. The method makes it possible to enhance the yield of PAc and to simplify processes for purifying PAc. The vaccine composition makes-it possible to internally easily absorb the protein antigen, PAc, in high efficiency and it also makes it possible to effectively increase the antibody titer observed after the administration thereof.

4 Claims, 2 Drawing Sheets

OTHER PUBLICATIONS

Iwaki et al., "Oral Immunization with Recombinant *Streptococcus lactis* Carrying the *Streptococcus mutans* Surface Protein Antigen Gene", *Infection and Immunity*, vol. 58, No. 9, (1990) pp. 2929–2934.

Lee et al., "Molecular Cloning and Expression of a *Streptococcus mutans* Major Surface Protein Antigen, P1 (I/II), in *Escherichia coli*", *Infection and Immunity*, vol. 56, No. 8, (1988) pp. 2114–2119.

Murchison et al., "Transformation of *Streptococcus mutans* with Chromosomal and Shuttle Plasmid (pYA629) DNAs", *Infection and Immunity*, vol. 54, No. 2, (1986) pp. 273–282.

N. Okahashi, et al., "Molecular characterization of a surface protein antigen from serotype *c Streptococcus mutan*, implicated in dental caries", *Molecular Microbiology*, vol. 3, pp. 673–678 (1989).

N. Okahashi et al., "Cloning of a surface protein antigen gene from serotype *c Strepococcus mutans*", vol. 3, pp. 221–228, (1989).

"Characterisation of Antigens Extracted From Cells and Culture Fluids of *Streptococcus Mutans* Serotype c", M. W. Russell and T. Lehner, Archs oral Biol., vol. 23, pp. 7–15, Pergamon Press, 1978.

METHOD FOR PREPARING VACCINE FOR DENTAL CARIES AND VACCINAL COMPOSITIONS FOR DENTAL CARIES USED AS NASAL DROP

BACKGROUND OF THE INVENTION

The present invention relates to a method for preparing a vaccine for dental caries, a novel variant of *Streptococcus mutans* GS-5 as well as a vaccinal composition for dental caries which is used as nasal drops.

*Streptococcus mutans* group is the most crucial pathogenic factor in dental caries in human beings and animals. The *S. mutans* group is divided into 7 species depending on the characteristics of their DNA's and *S. mutans* of serotype c, which is most closely related to human dental caries, posesses, on its surface, substances having various antigenicities such as serotype-specific polysaccharide antigens, lipoteichoic acid and protein antigens.

One of these substances present on the bacterial cell surface, a protein antigen having a molecular weight of about 190,000 determined by SDS polyacrylamide gel electrophoresis, is a fine fibrous structure called fimbriae. This protein antigen is known variously as I/II, B, P1 and IF and it does not yet have a uniform name. Thus, this protein antigen is herein called PAc (protein antigen serotype c).

The protein antigen of *S. mutans* has thus come to atract much interest in connection with development of a vaccine for dental caries. For instance, Japanese Patent Un-examined Published Application (hereunder referred to as "J.P. KOKAI") No. Sho 56-501362 proposes the use of the antigen I/II posessing specific properties as a vaccine for dental caries and J.P. KOKAI No. Sho 58-164518 discloses a vaccine for preventing the decay of teeth. The vaccine comprises, as an antigen, the component of bacterial cells of microorganisms belonging to genus Streptococcus or an extract thereof.

However, even if *S. mutans* is cultured in 10 liters of a culture medium and PAc is extracted therefrom, only several mg of PAc can be recovered. Thus, this technique cannot be put to practical use. In addition, the purification process for removing impurities from the resulting culture medium requires a great deal of labor and time since the concentration of PAc in the culture medium is very low.

Under such circumstances, the inventors of this invention have tried to insert a PAc-expressing gene(pac gene) of *S. mutans* into a host such as *E. coli* (*Escherichia coli*) or *S. milleri* (a species of Streptococcus) to thus make the host cells produce rPAc. However, no increase in yield was achieved because the gene was integrated into the bacteria of different species and rPAc was not externally secreted. In this respect, the term "rPAc" herein means PAc obtained through gene recombination (recombinant PAc) and it is a protein having a structure substantially identical with that of PAc.

Moreover, the inventors linked the pac gene to a plasmid-shuttle vector which can proliferate in both *E. coli* and Streptococcus host cells and inserted it into a *S. mutans* GS-5 strain which cannot express PAc. The results are reported in Review of Nippon Dentistry Society, 1989, No. 555. However, this method suffers from various problems. For instance, after insertion of the pac gene into the cells of the GS-5 strain, it is sometimes observed that the plasmid carrying the gene is left out of the resulting recombinant bacterial cells and thus the variant stops the production of PAc and the products are insufficient in their uniformity.

On the other hand, there have been known a protective vaccine for dental caries which contains the foregoing protein antigen, i.e., PAc and the vaccine has been used through injection or oral administration.

However, if immunization is carried out by injection via skin, muscle or veins, local inflammation or even functional disorders may possibly be caused. In addition, since the injection is accompanied by pain, it is difficult to immunize an infant or a child through injection and patients are in general reluctant to have a vaccine injected at certain portions such as, for instance, near the parotid. Furthermore, it is difficult to increase the antibody titer in saliva by the administration through injection.

Moreover, if it is orally administered, it may be digested in the stomach. Also, oral administration is liable to causes immune tolerance and consequent loss of response to the corresponding antigen. Besides, a high antibody titer cannot be achieved by the oral immunization.

SUMMARY OF THE INVENTION

An object of the present invention is to provide a method for preparing a vaccine for dental caries which makes it possible to enhance the yield of PAc and to simplify processes for purifying PAc as well as a variant of *S. mutans* GS-5 in which a pac gene is integrated into its chromosomal gene.

Another object of the present invention is to provide a vaccine composition whose component, the protein antigen PAc, is internally easily absorbed, in high efficiency, by a subject for immunization.

A further object of the present invention is to provide a vaccine composition capable of effectively increasing the antibody titer in a subject for immunization after the administration thereof and capable of sufficiently showing its vaccination effect.

These and other objects of the present invention will be apparent from the following description and Examples.

The method for preparing a vaccine for dental caries comprises the step of culturing a variant of an *S. mutans* GS-5 strain in which a protein antigen (PAc)-expressing gene (pac gene) is integrated into its chromosomal gene, the pac gene being produced on the surface of cells of oral *Streptococcus mutans* or it being extracellularly produced by the microorganism and having a molecular weight ranging from about 170,000 to 220,000.

The novel strain (*Streptococcus mutans* GS-9 (K-3) strain; FERM BP-2437) of the present invention was established through genetic engineering. More specifically, it was established by integrating the pac gene into the chromosomal gene of host cells, oral Streptococcus: *Streptococcus mutans*, to transform the host cells to thus substantially improve their productivity of PAc. The strain *Streptococcus mutans* GS-5 (K-3) was deposited as FERM BP-2437 at the Fermentation Research Institute in Japan on May 24, 1989.

The preventive vaccine for dental caries of the present invention comprises the protein antigen (PAc) which is produced on the surface of the cells of oral *Streptococcus mutans* or extracellularly produced by the microorganism. The composition is used in the form of a nasal drop which is intranasally applied.

The preventive vaccine for dental caries for nasal drop may further comprise a surfactant, cholera toxin B subunit or a bile acid or a derivative thereof.

DESCRIPTION OF THE PREFERRED EMBODIMENTS

Figure 1:
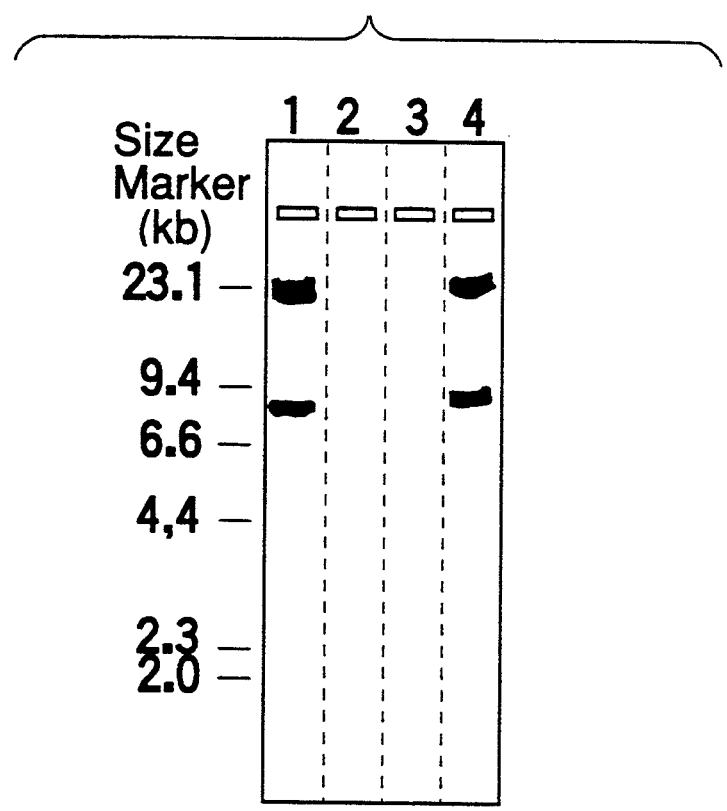
FIG. 1 is a diagram for illustrating the result of agarose electrophoresis of a plasmid-containing fraction. In the electrophoresis diagram, lane 1 illustrates the plasmid pSM1 (cyclic plasmid): lane 2 illustrates the plasmid-containing fraction of the GS-5 strain; lane 3 illustrates the plasmid-containing fraction of GS-5 (K-3) strain; and lane 4 illustrates the plasmid-containing fraction of GS-5 (K-9) strain.
Figure 2:
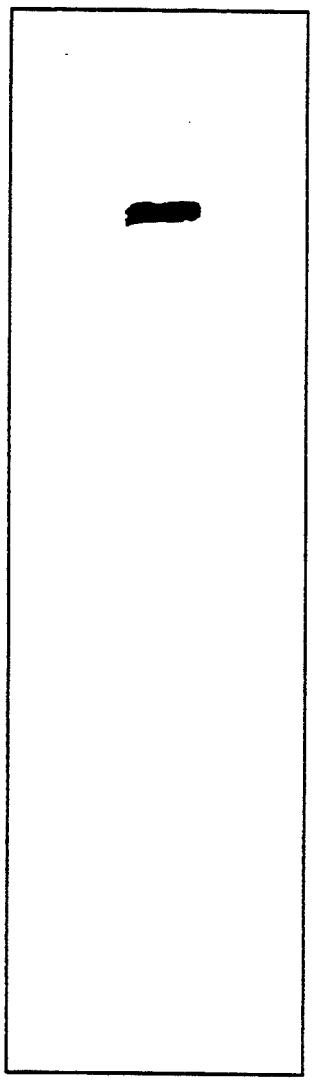
FIG. 2 is a diagram for showing the results of the Southern blot analysis of a chromosomal DNA using a $^{32}P$-labeled erythromycin-resistant gene, Bam HI fragment, as a probe. In the Southern blot analysis, lane 1 represents the Eco RI fragment of chromosomal DNA of the GS-5 strain; lane 2 represents the Eco RI fragment of chromosomal DNA of the GS-5 (K-3) strain; and lane 3 represents the Eco RI fragment of chromosomal DNA of the GS-5 (K-9) strain.

In the present invention, the *S. mutans* GS-5 strain is employed as host bacteria, while any donor bacteria may be used so far as they are strains belonging to species *S. mutans* capable of producing PAc and preferred are, for instance, strains of c serotype, e serotype and f serotype. Thus, optimum suppression of change in the structure of the rPAc produced can be realized by selecting host and donor bacteria from those belonging to the same species.

The *S. mutans* GS-5 strain is a known strain of *S. mutans* which is incapable of producing PAc and is preserved at various research institutes such as universities. The applicant of this invention deposited it with the Fermentation Research Institute (FRI) under an accession number of FERM BP-2436 under a designation of *Streptococcus mutans* GS-5 strain so that a third party can easily obtain it. The strain *Streptococcus mutans* GS-5 strain was deposited as FERM BP-2436 at the Fermentation Research Institute in Japan on May 24, 1989.

Examples of the donor bacteria used in the present invention include *Streptcoccus mutans* NCTC 10449, *Streptococcus mutans* MT8148, *Streptococcus mutans* Ingbritt, *Streptococcus mutans* MT6, *Streptococcus mutans* JC2, *Streptococcus mutans* MT118, *Streptococcus mutans* C67-1, *Streptococcus mutans* OMZ70, *Streptococcus mutans* MT6801, *Streptococcus mutans* JC 1-5, *Streptococcus mutans* ATCC 33477, *Streptococcus mutans* SE11, *Streptococcus mutans* OMZ175, *Streptococcus mutans* MT557, *Streptococcus mutans* P2 and *Streptococcus mutans* PK-1.

With the use of such donor bacteria, a gene which encodes PAc is inserted into the chromosome of the *Streptococcus mutans* GS-5 strain in a manner conventionally known in the art and thus the *Streptococcus mutans* GS-5 (K-3) strain of the present invention can be obtained. In this process, as the vector (plasmid for transferring PAc), there may be used, for instance, shuttle vectors pSA3 and pVA981 and as restriction enzymes for cleavage, there may be used, for instance, Bam HI, Sph I, Bgl II, Eco RI, Eco T14I, Hind III, Pst I and Sac I.

In the present invention, examples of the genes which encode the protein antigen (PAc) having a molecular weight ranging from about 170,000 to 220,000 preferably 180,000 to 210,000, include base sequences which encode the fragment substantially comprising 1,565 amino acid residues from the initiation codon (ATG) to the termination codon (TGA) of the following base sequence and fragments thereof. In addition, it is also possible to use base sequences in which a part thereof is replaced with other bases or one or more of the bases are deleted and which exhibit antigenicity substantially identical with that of PAc.

| Pos (L) | 1 | 2 | 3 | 4 | 5 | 6 | 7 | 8 | 9 | 10 | 11 | 12 | 13 | 14 | 15 | 16 | Pos (R) |
|---|---|---|---|---|---|---|---|---|---|---|---|---|---|---|---|---|---|
| 47 | T | TTG | TGC | TTT | AGA | ATT | AAT | GTT | GGA | TAA | AGT | GTG | GAG | TTT | GTC | CTC | 46 |
| 95 | GAA | TTG | TAG | CAG | CGA | TTG | AAT | GTG | TTT | ATA | ATT | CTG | ATT | CAG | ACA | TTA | 94 |
| 143 | GTT | TTT | ATT | ACG | TAT | TCA | AAA | ATT | AAA | TTG | CGA | TAT | TAT | GAC | ACA | AAT | 142 |
| 191 | TTT | TTA | ACG | TTT | GGA | ATG | TAT | ATA | AAA | TTG | GGA | TTG | TTC | AGA | AGT | TTT | 190 |
| 239/14 | ATT/Ile | AGT/Ser | AAA/Lys | ATG/Met | AAA/Lys | TAC/Tyr | AGT/Ser | GTT/Val | GAA/Glu | TTT/Phe | AAA/Lys | GGT/Gly | TAT/Tyr | CGT/Arg | AGT/Ser | AAA/Lys | 238/13 |
| 287/30 | TCT/Ser | GTA/Val | GCA/Ala | ACA/Thr | CAA/Gln | TGT/Cys | GTT/Val | GCT/Ala | CTA/Leu | GAT/Asp | ACG/Thr | GTA/Val | GCA/Ala | GTA/Val | ACT/Thr | AAT/Asn | 286/29 |
| 335/46 | GAT/Asp | GTA/Val | GAT/Asp | ACT/Thr | CAA/Gln | AAG/Lys | GTA/Val | GTT/Val | TTT/Phe | GAT/Asp | TTT/Phe | GCC/Ala | ACA/Thr | AAT/Asn | CCA/Pro | AGA/Arg | 334/45 |
| 383/62 | AAT/Asn | TTG/Leu | CCA/Pro | GAT/Asp | CAA/Gln | CTT/Leu | ATT/Ile | GGA/Gly | GGG/Gly | AGT/Ser | GGA/Gly | ACA/Thr | ACG/Thr | GCT/Ala | GAA/Glu | ACT/Thr | 382/61 |
| 431/78 | CAA/Gln | ACC/Thr | AAG/Lys | CTG/Leu | CAA/Gln | AGA/Arg | CAA/Gln | AGT/Ser | ATG/Met | CAT/His | ATT/Ile | GAA/Glu | TAC/Tyr | TCT/Ser | CCT/Pro | AAA/Lys | 430/77 |
| 479/94 | ACT/Thr | GAT/Asp | CTT/Leu | GAT/Asp | ATT/Ile | GCA/Ala | GCT/Ala | GAT/Asp | ATG/Met | GAT/Asp | ATC/Ile | GCT/Ala | TCT/Ser | TCG/Ser | GTC/Val | AAT/Asn | 478/93 |
| 527/110 | GTC/Val | CAA/Gln | GAT/Asp | GCA/Ala | TAT/Tyr | GCT/Ala | GTT/Val | ACT/Thr | GTT/Val | AAG/Lys | GTT/Val | GCA/Ala | GCT/Ala | AAT/Asn | GGT/Gly | GAA/Glu | 526/109 |
| 575/126 | GAA/Glu | GAG/Glu | CAG/Gln | TAT/Tyr | GCA/Ala | AAT/Asn | AAA/Lys | AGT/Ser | GGA/Gly | GCT/Ala | ACT/Thr | CAT/His | GAA/Glu | AAA/Lys | ACA/Thr | CAA/Gln | 574/125 |
| 623/142 | GCT/Ala | CAG/Gln | ATT/Ile | GCA/Ala | AAT/Asn | GCT/Ala | GCA/Ala | GAT/Asp | ATA/Ile | AAA/Lys | CAA/Gln | ACA/Thr | ACA/Thr | GCA/Ala | CCT/Pro | AAA/Lys | 622/141 |
| 671/158 | GCT/Ala | AAT/Asn | CAA/Gln | GCA/Ala | TAT/Tyr | GCA/Ala | ATG/Met | ATC/Ile | GAT/Asp | AAA/Lys | ACC/Thr | AAG/Lys | CAT/His | GCT/Ala | GCA/Ala | GTC/Val | 670/157 |
| 719/174 | AAA/Lys | GAA/Glu | CAG/Gln | TAT/Tyr | GCT/Ala | GAT/Asp | GCA/Ala | AGT/Ser | GCT/Ala | AAT/Asn | GAA/Glu | TAC/Tyr | GGT/Gly | GAG/Glu | GCA/Ala | AAA/Lys | 718/173 |
| 767/190 | CGC/Arg | GAA/Glu | CAG/Gln | TAT/Tyr | GCT/Ala | GAT/Asp | GCA/Ala | AGT/Ser | TTA/Leu | ACA/Thr | CAA/Gln | ACC/Thr | AAA/Lys | ACC/Thr | GCT/Ala | AAA/Lys | 766/189 |
| 815/206 | TTG/Leu | GCT/Ala | CAA/Gln | TAT/Tyr | GCT/Ala | CAA/Gln | AAT/Asn | AAT/Asn | GCC/Ala | GTT/Val | GCT/Ala | CAT/His | GCT/Ala | AAT/Asn | AAT/Asn | GCT/Ala | 814/205 |
| 863/222 | GCC/Ala | AAT/Asn | CAA/Gln | GCA/Ala | TAT/Tyr | GCC/Ala | AAA/Lys | CAA/Gln | GCA/Ala | CTT/Leu | ACA/Thr | CAG/Gln | TAT/Tyr | TAT/Tyr | GCT/Ala | GAA/Glu | 862/221 |
|  |  |  |  |  |  |  |  |  |  |  |  |  |  |  |  |  | 910/237 |

| | | | | | | | | | | | |
|---|---|---|---|---|---|---|---|---|---|---|---|
| 911<br>238 | CTG<br>Leu | AAA<br>Lys | CGT<br>Arg | GTT<br>Val | CAG<br>Gln | GAA<br>Glu | GCT<br>Ala | AAT<br>Asn | GCA<br>Ala | GCC<br>Ala | AAA<br>Lys | GCT<br>Ala | TAT<br>Tyr | GAT<br>Asp | 958<br>253 |
| 959<br>254 | ACT<br>Thr | GCT<br>Ala | GTA<br>Val | GCA<br>Ala | CAG<br>Gln | AAT<br>Asn | AAT<br>Asn | GCC<br>Ala | ACA<br>Thr | AAT<br>Asn | GAA<br>glu | ATT<br>Ile | GCT<br>Ala | GCC<br>Ala | 1006<br>269 |
| 1007<br>270 | AAT<br>Asn | GAA<br>Glu | GAA<br>Glu | ATT<br>Ile | AGA<br>Arg | CGC<br>Arg | AAA<br>Lys | ACG<br>Thr | GCC<br>Ala | AAA<br>Lys | GCT<br>Ala | TAT<br>Tyr | GAG<br>Glu | 1054<br>285 |
| 1055<br>286 | ACT<br>Thr | AAG<br>Lys | TTA<br>Leu | GCT<br>Ala | CAA<br>Gln | TAT<br>Tyr | CAA<br>Gln | CTA<br>Leu | AAG<br>Lys | CGT<br>Arg | GTT<br>Val | CAG<br>Gln | TAT<br>Tyr | CAG<br>Gln | 1102<br>301 |
| 1103<br>302 | AAT<br>Asn | GCC<br>Ala | GCA<br>Ala | AAC<br>Asn | GAA<br>Glu | GAC<br>Asp | TAT<br>Tyr | GCT<br>Ala | AAT<br>Asn | AAA<br>Lys | GCA<br>Ala | GCC<br>Ala | TAT<br>Try | CAA<br>Gln | 1150<br>317 |
| 1151<br>318 | ACA<br>Thr | GAG<br>Glu | CTT<br>Leu | CGT<br>Arg | GTT<br>Val | GAA<br>Glu | CAA<br>Gln | GCT<br>Ala | GCG<br>Ala | TTG<br>Leu | ACC<br>Thr | GCT<br>Ala | GCG<br>Ala | ACC<br>Thr | 1198<br>333 |
| 1199<br>334 | TAT<br>Tyr | GAA<br>Glu | GCA<br>Ala | GTA<br>Val | ATT<br>Ile | GCA<br>Ala | AAT<br>Asn | AAA<br>Lys | GCG<br>Ala | GAT<br>Asp | GCA<br>Ala | GCA<br>Ala | CTC<br>Leu | ACA<br>Thr | 1246<br>349 |
| 1247<br>350 | GCT<br>Ala | GAA<br>Glu | AAT<br>Asn | GCA<br>Ala | CTC<br>Leu | AAG<br>Lys | ATT<br>Ile | TAT<br>Tyr | AAT<br>Asn | GCG<br>Ala | AAT<br>Asn | GCT<br>Ala | GCG<br>Ala | ACT<br>Thr | 1294<br>365 |
| 1295<br>366 | TAT<br>Tyr | GAA<br>Glu | TAT<br>Tyr | GCA<br>Ala | CTC<br>Leu | AAG<br>Lys | AAC<br>Asn | CAA<br>Gln | TAT<br>Tyr | GCC<br>Ala | CAA<br>Gln | TTG<br>Leu | TTG<br>Leu | AAA<br>Lys | 1342<br>381 |
| 1343<br>382 | GCT<br>Ala | GCA<br>Ala | GCC<br>Ala | GCA<br>Ala | GCA<br>Ala | ACT<br>Thr | GCT<br>Ala | TAT<br>Tyr | GAC<br>Asp | GAG<br>Glu | GCT<br>Ala | GCA<br>Ala | GTG<br>Val | GCG<br>Ala | 1390<br>397 |
| 1391<br>398 | TAT<br>Tyr | CAA<br>Gln | AAT<br>Asn | GAG<br>Glu | CTC<br>Leu | GCA<br>Ala | AAA<br>Lys | GCA<br>Ala | GAC<br>Asp | CAA<br>Gln | AAG<br>Lys | AAA<br>Lys | ACC<br>Thr | ACA<br>Thr | 1438<br>413 |
| 1439<br>414 | GCA<br>Ala | GCT<br>Ala | TTA<br>Leu | GCA<br>Ala | AAT<br>Asn | GCT<br>Ala | CGC<br>Arg | ATT<br>Ile | GCC<br>Ala | CCA<br>Pro | AAT<br>Asn | GCG<br>Ala | GCT<br>Ala | ACT<br>Thr | 1486<br>429 |
| 1487<br>430 | CTC<br>Leu | ACA<br>Thr | TCT<br>Ser | GGA<br>Gly | AAT<br>Asn | ACT<br>Thr | CTT<br>Leu | AAA<br>Lys | GCA<br>Ala | GCT<br>Ala | GAT<br>Asp | GAT<br>Asp | AAA<br>Lys | 1534<br>445 |
| 1535<br>446 | GCT<br>Ala | GAT<br>Asp | TAT<br>Tyr | TAC<br>Tyr | GCA<br>Ala | AAA<br>Lys | GCA<br>Ala | TAT<br>Tyr | AAG<br>Lys | CTT<br>Leu | GAT<br>Asp | GCT<br>Ala | GCA<br>Ala | GCC<br>Ala | 1582<br>461 |
| 1583<br>462 | TAT<br>Tyr | CAA<br>Gln | GAA<br>Glu | GAC<br>Asp | TTA<br>Leu | AAT<br>Asn | CGC<br>Arg | GAC<br>Asp | TAT<br>Tyr | CCA<br>Pro | CCA<br>Pro | AAG<br>Lys | GCA<br>Ala | TAC<br>Tyr | 1630<br>477 |
| 1631<br>478 | GAT<br>Asp | GAA<br>Glu | GAA<br>Glu | ACT<br>Thr | TCT<br>Ser | GCA<br>Ala | AAA<br>Lys | GCA<br>Ala | ACA<br>Thr | GCA<br>Ala | GAA<br>Glu | CTT<br>Leu | GAA<br>Glu | CAT<br>His | 1678<br>493 |
| 1679<br>494 | AAT<br>Asn | AAT<br>Asn | GAA<br>Glu | GAC<br>Asp | GGA<br>Gly | CAA<br>Gln | AAC<br>Asn | AAT<br>Asn | AAC<br>Asn | TCT<br>Ser | TCT<br>Ser | CAA<br>Gln | AAA<br>Lys | GTC<br>Val | 1726<br>509 |
| 1727<br>510 | TAT<br>Tyr | GAT<br>Asp | CTT<br>Leu | CCA<br>Pro | GAG<br>Glu | TTA<br>Leu | TTG<br>Leu | TCT<br>Ser | ACA<br>Thr | GCG<br>Ala | GCA<br>Ala | GAT<br>Asp | GGG<br>Gly | AAG<br>Lys | 1774<br>525 |

| | | | | | | | | | | |
|---|---|---|---|---|---|---|---|---|---|---|
| 1775 Phe | CTT Leu | AAG Lys | GCT Ala | TCT Ser | GCT Ala | GTG Val | GAT Asp | GCT Ala | TTT Phe | AGC Ser | AAA Lys | ACT Thr | TCA Ser | 1822 541 |
| 1823 Lys | GCA Ala | AAA Lys | TAT Tyr | GAC Asp | CAA Gln | AAA Lys | ATT Ile | CAA Gln | TTA Leu | GAT Asp | GAT Asp | ATC Ile | 1870 557 |
| 1871 Thr | AAC Asn | TTA Leu | GAA Glu | CAA Gln | TCT Ser | AAT Asn | GAT Asp | GCT Ala | TCT Ser | ACG Thr | TCT Ser | CTT Leu | TAT Tyr | 1918 573 |
| 1919 Gly | AAT Asn | TTT Phe | GGT Gly | AAA Lys | GAT Asp | GGA Gly | GCT Ala | TCA Ser | GGC Gly | ACA Thr | GAG Glu | ACA Thr | CGC Arg | ATG Met | GTA Val | AAT Asn | 1966 589 |
| 1967 Ser | CAG Gln | GTT Val | CAA Gln | AAA Lys | GGT Gly | AAC Asn | AAT Asn | GTA Val | TTA Leu | CTA Leu | TAC Tyr | TCG Ser | GGC Gly | GTA Val | TCA Ser | TAT Tyr | GGT Gly | CAA Gln | AGC Ser | GGT Gly | CTT Leu | GCA Ala | 2014 605 |
| 2015 Thr | GCT Ala | CAA Gln | AAC Asn | TAC Tyr | TAT Tyr | ATT Ile | CAG Gln | TCT Ser | GCT Ala | GCT Ala | CCT Pro | TAT Tyr | AAT Asn | CAA Gln | AGC Ser | CTT Leu | 2062 621 |
| 2063 Ile | ATT Ile | TCA Ser | AAA Lys | ATT Ile | AAG Lys | TAT Tyr | CTG Leu | TGG Trp | TAT Tyr | TCT Ser | GTG Val | GAC Asp | ACC Thr | GAT Asp | AAA Lys | AAG Lys | TAT Tyr | TTT Phe | GAT Asp | 2110 637 |
| 2111 Gln | CAA Gln | GTT Val | CAA Gln | GCT Ala | AAG Lys | TTA Leu | TAT Tyr | ATT Ile | TTT Phe | GTT Val | CAG Gln | GGT Gly | GAA Glu | CGT Arg | TCC Ser | ACA Thr | TCT Ser | TTT Phe | 2158 653 |
| 2159 Ser | GGT Gly | GCT Ala | TCT Ser | TAT Tyr | TGG Trp | TAT Tyr | ACA Thr | ACT Thr | GAA Glu | GCT Ala | ACT Thr | AAA Lys | CCA Pro | CCA Pro | ATT Ile | 2206 669 |
| 2207 Asn | CTT Leu | AAT Asn | AAT Asn | ATT Ile | CAA Gln | CAC His | GAA Glu | GAA Glu | GAT Asp | AAA Lys | ATT Ile | CGC Arg | AAC Asn | ACA Thr | GAA Glu | 2254 685 |
| 2255 Ser | AGT Ser | AAT Asn | AAT Asn | AAT Asn | AAG Lys | TTT Phe | GGT Gly | TCA Ser | ACT Thr | CTT Leu | AGT Ser | TCT Ser | TCA Ser | CAT His | ATG Met | AAG Lys | 2302 701 |
| 2303 Lys | GAT Asp | ATT Ile | TCA Ser | GAG Glu | GCT Ala | GAT Asp | TAT Tyr | AAA Lys | ATG Met | AGT Ser | AGT Ser | AAA Lys | ATC Ile | 2350 717 |
| 2351 Ser | GGT Gly | TCT Ser | TCA Ser | GCT Ala | GGT Gly | GGT Gly | AAG Lys | GGC Gly | GGC Gly | CGT Arg | ACA Thr | ACA Thr | GAT Asp | 2398 733 |
| 2399 Thr | CTT Leu | AAT Asn | TTT Phe | ATG Met | GCA Ala | GAA Glu | CAG Gln | GGT Gly | GAT Asp | GAT Asp | ATG Met | CCA Pro | GAT Asp | 2446 749 |
| 2447 Lys | AAT Asn | CAA Gln | CAA Gln | ATT Ile | GAT Asp | ACA Thr | GGG Gly | AGT Ser | TGG Trp | ATT Ile | GGA Gly | GCT Ala | AAA Lys | 2494 765 |
| 2495 Ser | GCT Ala | GGA Gly | GGA Gly | GCT Ala | GCA Ala | AAT Asn | ATG Met | GCA Ala | GCG Ala | TAT Tyr | AAT Asn | GAT Asp | CCG Pro | AAC Asn | CCA Pro | CAT His | 2542 781 |
| 2543 Val | GTT Val | TAT Tyr | GTA Val | GCA Ala | TCT Ser | AAT Asn | GCA Ala | GCA Ala | CTG Val | CCT Ser | AGT Ser | CCA Pro | GTT Val | GAC Asp | 2590 797 |
| 2591 Met | ATG | CCT | GTT | AAG | CCT | GGT | ACT | GAT | AAT | GGC | AAG | GAT | GGC | CCA | AAA | AAT | 2638 |

| | Met | Pro | Val | Val | Pro | Gly | Lys | Asp | Asn | Thr | Asp | Gly | Lys | Lys | Pro | Asn | |
|---|---|---|---|---|---|---|---|---|---|---|---|---|---|---|---|---|---|
| 798 | | | | | | | | | | | | | | | | | 813 |
| 2639 | ATT | TGG | TAT | TCT | TTA | AAT | GGT | AAA | ATC | CGT | GCG | GTT | AAT | GTT | CCT | AAA | 2686 |
| 814 | Ile | Trp | Tyr | Ser | Leu | Asn | Gly | Lys | Ile | Arg | Ala | Val | Asn | Val | Pro | Lys | 829 |
| 2687 | GTT | ACT | AAG | GAA | AAA | CCC | ACA | CCT | CCG | GTT | AAA | CCA | ACA | GCT | CCA | ACT | 2734 |
| 830 | Val | Thr | Lys | Glu | Lys | Pro | Thr | Pro | Pro | Val | Lys | Pro | Thr | Ala | Pro | Thr | 845 |
| 2735 | AAA | CCA | ACT | TAT | GAA | ACA | GAA | AAG | CCA | CCA | ACA | CCG | GCA | CCA | GTA | GCT | 2782 |
| 846 | Lys | Pro | Thr | Tyr | Glu | Thr | Glu | Lys | Pro | Pro | Thr | Pro | Ala | Pro | Val | Ala | 861 |
| 2783 | CCA | AAT | GAG | GAG | TAT | CCA | ACA | GAG | CCG | CCA | ACA | AGG | GCA | ACA | GAT | CAA | 2830 |
| 862 | Pro | Asn | Glu | Glu | Tyr | Pro | Thr | Glu | Pro | Pro | Thr | Arg | Ala | Thr | Asp | Gln | 877 |
| 2831 | GCA | GAG | GAG | ACA | CCA | AAC | AAT | AAA | CCG | CCA | ACA | GAA | ACA | ACA | AAG | CCG | 2878 |
| 878 | Ala | Glu | Glu | Thr | Pro | Asn | Asn | Lys | Pro | Pro | Thr | Glu | Thr | Thr | Lys | Pro | 893 |
| 2879 | TTG | TAT | GAG | CAT | GTT | GTT | CCT | CCG | CCA | AGC | TAT | ACC | TAT | GAG | CCA | CCG | 2926 |
| 894 | Leu | Tyr | Glu | His | Val | Val | Pro | Pro | Pro | Ser | Tyr | Thr | Tyr | Glu | Pro | Pro | 909 |
| 2927 | CCG | ACA | GAA | GCA | CCT | GTT | CCG | GAG | GAG | GAA | CCA | CCC | GTT | GAT | ACA | AGC | 2974 |
| 910 | Pro | Thr | Glu | Ala | Pro | Val | Pro | Glu | Glu | Glu | Pro | Pro | Val | Asp | Thr | Ser | 925 |
| 2975 | ACC | TAT | GAA | ACA | GAA | CCA | ACA | TAT | CCA | GCT | ACA | CCT | GTT | GAT | AAC | GAA | 3022 |
| 926 | Thr | Tyr | Glu | Thr | Glu | Pro | Thr | Tyr | Pro | Ala | Thr | Pro | Val | Asp | Asn | Glu | 941 |
| 3023 | TAT | GAA | GCA | ACA | ACA | TAC | AAT | GAA | GCT | AAT | CTG | CCA | GCA | GCA | CCT | CAA | 3070 |
| 942 | Tyr | Glu | Ala | Thr | Thr | Tyr | Asn | Glu | Ala | Asn | Leu | Pro | Ala | Ala | Pro | Gln | 957 |
| 3071 | CCA | AAC | GCA | GAG | CCT | AAT | ACT | ACG | AAT | ACA | GTT | CCC | GAT | CCA | CCG | CCG | 3118 |
| 958 | Pro | Asn | Ala | Glu | Pro | Asn | Thr | Thr | Asn | Thr | Val | Pro | Asp | Pro | Pro | Pro | 973 |
| 3119 | ACT | GAT | TCT | GTT | TAT | CAA | GAT | CTT | CCA | GAG | CCT | TCT | ACA | GAT | TCT | ACT | 3166 |
| 974 | Thr | Asp | Ser | Val | Tyr | Gln | Asp | Leu | Pro | Glu | Pro | Ser | Thr | Asp | Thr | Thr | 989 |
| 3167 | GTT | CAT | TTC | AAT | TAC | AAT | TTT | AAA | CTA | GCT | GTC | TAT | CCG | CAG | TTG | AAG | 3214 |
| 990 | Val | His | Phe | Asn | Tyr | Asn | Phe | Lys | Leu | Ala | Val | Tyr | Pro | Gln | Leu | Lys | 1005 |
| 3215 | GAA | AAC | AGA | GAA | AAT | AAG | AAC | CAG | ATT | GAC | ACA | AAT | GTC | GAG | CAA | AAC | 3262 |
| 1006 | Glu | Asn | Arg | Glu | Asn | Lys | Asn | Gln | Ile | Asp | Thr | Asn | Val | Glu | Gln | Asn | 1021 |
| 3263 | AAA | CAA | CGT | GAA | GTT | AAG | TTT | TTC | CAG | CTG | GAC | ACA | GTA | AAC | CTG | GCT | 3310 |
| 1022 | Lys | Gln | Arg | Glu | Val | Lys | Phe | Phe | Gln | Leu | Asp | Thr | Val | Asn | Leu | Ala | 1037 |
| 3311 | GGA | TAT | GAT | CAA | ACT | CCT | GAA | TTC | TCC | TTT | GCT | ACT | CTC | CCA | GGC | TCT | 3358 |
| 1038 | Gly | Tyr | Asp | Gln | Thr | Pro | Glu | Phe | Ser | Phe | Ala | Thr | Leu | Pro | Gly | Ser | 1053 |
| 3359 | GGT | TAT | TAT | TTT | GAA | AAT | TTT | GAA | GCT | GTA | GCT | AGC | CCC | CTG | CCA | TTT | 3406 |
| 1054 | Gly | Tyr | Tyr | Phe | Glu | Asn | Phe | Glu | Ala | Val | Ala | Ser | Pro | Leu | Pro | Phe | 1069 |
| 3407 | GAT | GTC | TAT | TAT | GAT | AAT | ACA | GTC | ACC | GCA | AAG | ACT | AAG | GCA | GCA | ACT | 3454 |
| 1070 | Asp | Val | Tyr | Tyr | Asp | Asn | Thr | Val | Thr | Ala | Lys | Thr | Lys | Ala | Ala | Thr | 1085 |

| Pos (nt) | Pos (aa) | 1 | 2 | 3 | 4 | 5 | 6 | 7 | 8 | 9 | 10 | 11 | 12 | 13 | 14 | 15 | 16 | End nt | End aa |
|---|---|---|---|---|---|---|---|---|---|---|---|---|---|---|---|---|---|---|---|
| 3455 | 1086 | GCA Ala | ACT Thr | TTG Leu | GCT Ala | ACG Thr | TTT Phe | AAT Asn | GAT Asp | TTG Leu | ACT Thr | AAG Lys | TCA Ser | GTG Val | GCA Ala | | | 3502 | 1101 |
| 3503 | 1102 | ACG Thr | TAT Tyr | ATT Ile | ACA Thr | GTG Val | GTC Val | CTC Leu | GTT Val | CTT Leu | AAT Asn | GCT Ala | CCA Pro | GCA Ala | ACT Thr | | | 3550 | 1117 |
| 3551 | 1118 | TAT Tyr | AAT Asn | CCA Pro | TTC Phe | ACG Thr | CTC Leu | TTC Phe | GAT Asp | AAT Asn | GCT Ala | GGC Gly | GGC Gly | ATT Ile | AAA Lys | | | 3598 | 1133 |
| 3599 | 1134 | TCC Ser | AAT Asn | GTT Val | CGG Arg | GTG Val | ACA Thr | GTT Val | CCT Pro | AAA Lys | AAG Lys | GAT Asp | GAT Asp | CCA Pro | GAT Asp | | | 3646 | 1149 |
| 3647 | 1150 | AAT Asn | CCA Pro | AAT Asn | AAT Asn | TAT Tyr | AAT Asn | ACT Thr | CCA Pro | AAA Lys | AAG Lys | AAA Lys | ACA Thr | AAC Asn | GAA Glu | | | 3694 | 1165 |
| 3695 | 1166 | AAT Asn | GGC Gly | ATT Ile | GTT Val | GAT Asp | GGT Gly | GGT Gly | ACA Thr | AAG Lys | CTT Leu | GGT Gly | TCA Ser | ACG Thr | AAT Asn | | | 3742 | 1181 |
| 3743 | 1182 | TAT Tyr | TAT Tyr | GAT Asp | CTA Leu | CGG Arg | GAT Asp | TGG Trp | TAT Tyr | TAT Tyr | TAT Tyr | TAT Tyr | GAT Asp | CGC Arg | TCT Ser | | | 3790 | 1197 |
| 3791 | 1198 | TCA Ser | GCA Ala | GAT Asp | ACC Thr | ATT Ile | CAA Gln | TTA Leu | TTT Phe | GTG Val | TAT Tyr | GCA Ala | CCA Pro | CCA Pro | | | | 3838 | 1213 |
| 3839 | 1214 | GAA Glu | GAA Glu | GCG Ala | CTT Leu | GAA Glu | TTG Leu | GAT Asp | CAG Gln | TTG Leu | GTT Val | TTC Phe | ACA Thr | AGA Arg | GCT Ala | | | 3886 | 1229 |
| 3887 | 1230 | AAT Asn | GGT Gly | ATT Ile | GAA Glu | GTT Val | ACT Thr | GTT Val | GAT Asp | ACT Thr | GGA Gly | GGA Gly | ATT Ile | AAT Asn | CTT Leu | | | 3934 | 1245 |
| 3935 | 1246 | GAA Glu | GCA Ala | ATC Ile | GCC Ala | GAA Glu | CAA Gln | CAA Gln | AGT Ser | GAT Asp | GGT Gly | GGT Gly | ACT Thr | GCA Ala | ATT Ile | | | 3982 | 1261 |
| 3983 | 1262 | AGA Arg | CCT Pro | AAA Lys | GCT Ala | CAA Gln | AGA Arg | ATT Ile | GAT Asp | CTT Leu | GCC Ala | CCA Pro | CCA Pro | AGA Arg | GAA Glu | | | 4030 | 1277 |
| 4031 | 1278 | TTT Phe | TAT Tyr | GAT Asp | TAC Tyr | ATT Ile | ACT Thr | TTC Phe | TTG Leu | ATT Ile | AAT Asn | GAT Asp | ATT Ile | GTA Val | TCA Ser | | | 4078 | 1293 |
| 4079 | 1294 | CCA Pro | ATG Met | GCC Ala | AAT Asn | CCT Pro | ATG Met | CAA Gln | GGA Gly | GGA Gly | GGT Gly | TAT Tyr | AGT Ser | TAT Tyr | GAA Glu | | | 4126 | 1309 |
| 4127 | 1310 | AAT Asn | CAA Gln | ATC Ile | TAT Tyr | AAT Asn | TTT Phe | GGT Gly | GAT Asp | AAG Lys | GCA Ala | AAT Asn | AAT Asn | ATT Ile | ATC Ile | | | 4174 | 1325 |
| 4175 | 1326 | GTT Val | CTT Leu | AAT Asn | CCG Pro | GAT Asp | ATT Ile | GGT Gly | CAG Gln | GGT Gly | ACC Thr | GTA Val | TTA Leu | | | | | 4222 | 1341 |
| 4223 | 1342 | ACA Thr | GAT Asp | TAC Tyr | GTC Val | GCT Ala | TAC Tyr | CAA Gln | ATT Ile | GAT Asp | CAG Gln | ACT Thr | ATT Ile | CCA Pro | | | | 4270 | 1357 |
| 4271 | 1358 | CTT Leu | AAT Asn | ACA Thr | TAC Tyr | TAC Tyr | CGT Arg | TTG Leu | ATT Ile | GGT Gly | GGC Gly | ATC Ile | CCT Pro | GCA Ala | | | | 4318 | 1373 |

| | | | | | | | | | | | |
|---|---|---|---|---|---|---|---|---|---|---|---|
| 4319 | AAT Asn | CAC His | TCA Ser | GAA Glu | GAA Glu | CTC Leu | TTT Phe | TAC Tyr | AAT Asn | TTC Phe | TAT Tyr | GAT Asp | 4366 |
| 1374 | | | | | | | | | | | | 1389 |
| 4367 | CAA Gln | ACA Thr | GGA Gly | GAT Asp | CAC His | TAT Tyr | ACT Thr | CAG Gln | TAT Try | AAA Lys | TTT Phe | GTT Val | 4414 |
| 1390 | | | | | | | | | | | | 1405 |
| 4415 | GAT Asp | ATC Ile | ACT Thr | CTT Leu | AAA Lys | AAC Asn | GGT Gly | ATT Ile | ATC Ile | AAG Lys | GGT Gly | TCA Ser | 4462 |
| 1406 | | | | | | | | | | | | 1421 |
| 4463 | ACT Thr | CAG Gln | TAT Tyr | ACG Thr | ACA Thr | GCG Ala | GAA Glu | GAT Asp | ACC Thr | ACT Thr | GGT Gly | TTA Leu | 4510 |
| 1422 | | | | | | | | | | | | 1437 |
| 4511 | ATT Ile | AAG Lys | TTC Phe | AAG Lys | GAA Glu | GCC Ala | TTT Phe | CGT Arg | TCT Ser | AAA Lys | TCA Ser | ACA Thr | 4558 |
| 1438 | | | | | | | | | | | | 1453 |
| 4559 | TTC Phe | CAA Gln | GCT Ala | AAG Lys | CAA Gln | GCC Ala | TTT Phe | CAA Gln | AAA Lys | AAT Asn | ATT Ile | GCC Ala | 4606 |
| 1454 | | | | | | | | | | | | 1469 |
| 4607 | TTT Phe | GAA Glu | AAT Asn | CAA Gln | GAA Glu | TAT Tyr | ATC Ile | CGT Arg | GAT Asp | TCA Ser | GGT Gly | ACT Thr | 4654 |
| 1470 | | | | | | | | | | | | 1485 |
| 4655 | AAT Asn | ACA Thr | GTG Val | GTA Val | AGT Ser | ACT Thr | CTG Leu | CGT Arg | GGG Gly | GCA Ala | GAC Asp | AGT Ser | 4702 |
| 1486 | | | | | | | | | | | | 1501 |
| 4703 | CCG Pro | CAA Gln | GAT Asp | ACT Thr | TCA Ser | TCA Ser | CCG Pro | ATG Met | CCT Pro | ACT Thr | ATT Ile | ACT Thr | 4750 |
| 1502 | | | | | | | | | | | | 1517 |
| 4751 | CCT Pro | CAA Gln | TCA Ser | ACT Thr | GCT Ala | TAT Tyr | CAG Gln | CCA Pro | ACT Thr | GTT Val | GAA Glu | AGT Ser | 4798 |
| 1518 | | | | | | | | | | | | 1533 |
| 4799 | AAT Asn | ACG Thr | GGA Gly | GTA Val | ACA Thr | AAC Asn | AGT Ser | GCT Ala | TAT Tyr | ATG Met | GGT Gly | TAC Tyr | 4846 |
| 1534 | | | | | | | | | | | | 1549 |
| 4847 | GGC Gly | TTA Leu | GTT Val | ACT Thr | AGT Ser | TTT Phe | CTT Leu | TTG Leu | CTT Leu | GGT Gly | AAG Lys | AAA Lys | 4894 |
| 1550 | | | | | | | | | | | | 1565 |
| 4895 | TGA *** | CAG | CAT | AGA | TAC | ATT | TAC | AGA | ATT | AAA | AGC | CCA Pro | 4942 |
| 1566 | | | | | | | | | | | | |
| 4943 | AAA | TCA | CAG | ATT | GAG | CTT | TTA | TCT | ATT | CAT | TTG | ATT Ile | 4990 |
| 4991 | AAT | AAC | TAG | CCT | ATC | TTT | GTT | CTA | TTA | AAA | CAG | TTA Leu | 5038 |
| 5039 | AGG | AAT | ATC | ATT | AAC | CAA | TTT | TAG | CAA | GAT | CAT | TGA | 5086 |
| 5087 | TTT | AAC | TAT | CTT | TCT | TAA | AGA | TAA | AAT | ATA | GTG | TAG | 5134 |
| 5135 | ATT | ACT | AAC | GTT | TGA | CAC | GGT | CTT | | | | | |

Since the strain GS-5 (K-3) of the present invention is obtained by integrating the pac gene into the chromosonal DNA of the strain GS-5, the leaving out of the pac gene from the strain is hardly caused and the strain extracellularly produces rPAc in high yield.

The site of the chromosomal DNA of the strain on which the pac gene exists can be confirmed by the Southern blot technique or the like. Therefore, rPAc can be obtained in high efficiency by isolating such a strain and culturing the same. Moreover, the processes for purifying rPAc can be substantially simplified since the content of rPAc in the culture supernatant is very high. The resulting rPAc can be used as a vaccine for dental caries in a variety of forms.

The strain GS-5 (K-3) of the present invention can be cultured, for instance, in the following manner. 37 g of a brain heart infusion medium is dissolved in 1l of distilled water, then the resulting solution is sterilized at 121° C. for 20 minutes and 1 ml of a 5 mg/ml erythromycin solution which has been filtered and sterilized in advance is added to and mixed with the foregoing solution to give a culture medium. The culture medium is dispensed in 10 ml portions into 24 ml sterilized test tubes, the strain GS-5 (K-3) is inoculated into each test tube and cultured at 37° C. for 18 hours to thus give a seed cultue liquid. 100 ml of the seed culture liquid is added to a 2l volume flask in which 1l of a culture medium having the same composition has been added and cultured at 37° C. for 18 hours to thus give a culture medium containing microorganisms. The medium is centrifuged at 10,000 X g for 15 minutes to obtain a culture supernatant.

The purification of rPAc from the culture supernatant can be performed by various means. For instance, there can be used gel filtration methods such as those in which dextrans or agaroses are employed as a stationary phase; ion-exchange techniques such as those in which AE, DEAE, QAE, CM, SP, Phospho or the like is used as an ion-exchange resin; hydrophobic chromatography techniques such as those in which Octyl Sepharose, Phenyl Sepharose or the like is employed as stationary phase; and affinity chromatography techniques.

The resultant vaccines for dental caries are administered, for instance, orally or via subcutaneous injection. The dose thereof desirably ranges from about 10 μg to about 50 mg and preferably 10 μg to 10 mg and the optimum dose thereof is 1 mg.

The bacteriological properties of the *Streptococcus mutans* GS-5 (K-3) (FERM BP-2437) are as follows. The determination of these bacteriological properties and the classification are performed according to the methods disclosed in Bergey's Manual of Systematic Bacteriology, 1986, 2.

A. Morphological Features

When the strain was cultured in a brain-heart infusion medium at 37° C. for 2 days, the following morphological features were observed:

1) Shape and Size of the Cell

It is a coccus; the size thereof ranges from 0.5 to 0.75 μm and it forms linkages.

2) Polymorphism: none.
3) Motility: none.
4) Spore: none.
5) Gram Staining: positive.
6) Resistance to Acid: negative.

B. Culturing Properties (Cultivability) 1) Brain heart infusion agar plate culture:

The strain grows at pH ranging from 7.0 to 7.4 and forms circular, flat, entire colonies. The surface of these colonies is smooth and glossy and the color thereof is yellowish white or pale brown.

2) Brain heart infusion agar slant culture:

It grows at pH ranging from 7.0 to 7.4 on wide belt-shaped regions and forms glossy yellowish white or pale brown colored colonies.

3) Brain heart infusion liquid culture:

It grows at pH ranging from 7.0 to 7.4, but does not form pellicles and the turbidity of the culture medium is uniform.

4) Broth gelatin stab culture:

The culture medium is not liquefied at all.

5) Litmus milk:

It grows sufficiently, produces acids and causes coagulation of milk.

C. Physiological Properties

1) Reduction of nitrates: negative.
2) Denitrification reaction: negative.
3) MP test: positive.
4) VP test: positive.
5) Production of indole: negative.
6) Formation of hydrogen sulfide: negative.
7) Hydrolysis of starches: negative.
8) Use of citric acid: It does not use citric acid in either Koser's or Christensen's mediums.
9) Use of inorganic nitrogen: It does not use either nitrates or ammonium salts.
10) Generation of dyes: negative.
11) Urease: negative.
12) Oxidase: negative.
13) Catalase: negative.
14) Range of growth conditions:

The growth temperature ranges from 33° to 38° C. (optimum temperature: 37° C.). The growth pH thereof ranges from 6.0 to 7. 4.

15) Behavior against oxygen: facultative anaerobic.
16) O-F test: positive.
17) Generation of acids and gases from sugars.: It produces acids from D-glucose, D-mannose, D-fructose, D-galactose, malt sugar (maltose), cane sugar (sucrose), trehalose, D-sorbit and D-mannit, but does not generate gases at all. It generates neither acids nor gases from L-arabinose, D-xylose, inosit, glycerin and starches.

D. Other Miscellaneous Characteristics

1) Decomposition of arginine: negative.
2) Hemolysis type: γ hemolysis.
3) Resistance to sodium chloride: resistant to 4% sodium chloride solution.
4) Other properties found necessary: It hydrolyzes esculin and is resistant to 2 U/ml of bacitracin. It generates acids from inulin, D-raffinose and D-melibiose. It synthesizes glucan from sucrose.

The aforesaid properties can be summarized as follows: the strain is a gram positive Streptococcus which produces acids from inulin, D-raffinose, D-melibiose and D-sorbit, which does not hydrolyze arginine and which is resistant to bacitracin. Thus, it can be concluded that the microorganism is a strain belonging to species *Streptococcus mutans*.

In the vaccine of the present invention, it is also possible to use the cortex of the cells of the foregoing *S. mutans* or those which are extracellularly produced by the strain in addition to the protein antigen (PAc) obtained by the method described above. More specifically, PAc is a protein present on the cortex of the cell bodies, but the strain secretes PAc extracellularly. Therefore, the easiest way for the preparation of the vaccine is to use the culture medium obtained after the cultivation of *S. mutans*. For instance, *S. mutans* strain ATCC 25175 is cultured in an outer solution obtained by dialyzing a brain-heart infusion culture medium (available from BBL Company, Difco Company etc.), the resulting culture supernatant is subjected to a salting out process carried out at a saturated ammonium sulfate concentrtion (60%), the product salted out is dissolved in a 50 mM Tris-hydrochloric acid buffer and then dialyzed against the same buffer. Subsequently, the preparation thus obtained is added to a column packed with DEAE Sephacel (available from Pharmacia Co., Ltd.) which has been equilibrated with the same buffer and elution is performed by a linear concentration gradient of NaCl ranging from 0 to 0.5 M whereby PAc is eluted at an NaCl concentration of about 0.2 M. The resulting PAc-containing fractions are pooled, concentrated and subjected to gel filtration using Sepharose CL-6B to obtain purified PAc-containing fractions which are used as the purified PAc.

Further, proteins equivalent to PAc and rPAc obtained from strains belonging to species *Streptococcus mutans* other than the *S. mutans* serotype c, which produce protein antigens common to PAc are also included in the scope of this invention and hence may be used in the vaccine composition of the present invention.

In the present invention, to the purified PAc there may optionaly be added carriers, diluents, or other additives such as preservatives, humectants, binders, adjuvants and agents for accelerating absorption to obtain pharmaceutical preparations used as nasal drops.

The amount of PAc to be added to the vaccine composition suitably ranges from 0.05 to 50 mg/0.2ml and preferably 0.5 to 20 mg/0.2 ml.

The vaccine composition of the present invention is preferably administered in an amount ranging from 0.05 to 0.6 m l/dose. Moreover, the vaccine composition of the present invention is suitably administered 2 or more times and preferably 2 to 6 times to achieve the desired immunization effect.

The vaccine composition of the present invention makes it possible to intranasally immunize a subject. Therefore, it may be easily administered even to many persons and the administration thereof is not accompanied by pain. Since at least two administrations are in general required for achieving the desired immunization effect, simplicity and the possibility of administration without pain are very important for the immunization procedures.

The antibody titer of the vaccine composition of the present invention can effectively be increased by the addition of cholera toxin B, a surfactant or a bile acid or a derivative thereof to the composition for nasal drops.

The amount of the cholera toxin B to be added to the composition suitably ranges from 10 $\mu$g to 20 mg/0.2 ml and preferably 50 $\mu$g to 10 mg/0.2 ml of the vaccine composition.

The surfactants may be anionic surfactants, cationic surfactants, nonionic surfactants and/or amphoteric surfactants, in particular cationic surfactants are preferred. These surfactants may be used alone or in any combination. The amount of the surfactants to be incorporated into the vaccine composition suitably ranges from 0.01 to 10% by weight, preferably 0.1 to 5% by weight on the basis of the total eight of the composition for anionic and nonionic surfactants and suitably ranges from 0.001 to 1.0% by weight and preferably 0.01 to 0.5% by weight on the basis of the total weight of the composition for cationic surfactants.

Examples of the anionic surfactants are carboxylic acid salts such as higher fatty acid salts (soaps) and N-acylamino acid salts of, for instance, lauroyl sarcosinate; sulfuric acid ester salts such as alkyl sulfates (for instance, lauryl sulfate), alkyl ether sulfates (for instance, polyoxyethylene alkyl ether sulfates) and fatty acid monoglyceride sulfates; alkane sulfonate; sulfosuccinates such as sodium dioctyl sulfosuccinate; N-acylsulfonates, fatty acid monoglyceride sulfonates and $\alpha$-sulfofatty acid ester salts; alkyl phosphoric acid salts; and alkyl ether phosphoric acid salts.

Examples of the cationic surfactants are quaternary ammonium salts such as benzethonium chloride, benzalkonium chloride, cetyl pyridinium chloride, chlorohexyzine gluconate and chlorohexyzine. hydrochloride.

Examples of the nonionic surfactants are polyoxyethylene alkyl ethers, polyoxyethylene alkyl phenyl ethers (such as Triton X-100), polyoxyethylene fatty acid esters, polyoxyethylene sorbitan fatty acid esters (such as Tween 20 and Tween 80), polyoxyethylene (hardened) castor oil, polyoxyethylene glycerin fatty acid esters and polyoxyethylene-polyoxypropylene copolymers.

Among the surfactants listed above, preferred are nonionic surfactants such as polyoxyethylene octyl ether, polyoxyethylene nonyl ether, polyoxyethylene lauryl ether, polyoxyethylene stearyl ether, polyoxyethylene cetyl ether, polyoxyethylene octylphenyl ether and Triton X100, whose average molar number of added ethylene oxide ranges from 5 to 30; cationic surfactants such as benzethonium chloride and benzalkonium chloride; and anionic surfactants such as sodium lauryl sulfate and potassium lauryl sulfate.

Examples of bile acids usable in the present invention include etiobilianic acid, etioallobilianic acid, etianic acid, 3-hydroxy-nor-5$\alpha$-cholanic acid, dehydrocholic acid, cilianic acid, 12-ketocholanic acid, lithocholic acid, deoxycholic acid, chenodeoxycholic acid, cholic acid and cholanic acid. In addition to these compounds, it is also possible to use derivatives and salts such as sodium and potassium salts thereof and sodium and potassium salts of the derivatives. Among these derivatives of bile acids, preferred are amide compounds of bile acids with amino acids or aminosulfonic acids and their sodium and potassium salts are also suitably employed in the present invention. Examples of such amino acids and aminosulfonic acids are glycine, serine, asparagine, aspartic acid and taurine. Among these, particularly preferred are sodium taurocholate, sodium glycocholate, sodium cholate and sodium deoxycholate.

The amount of these bile acids or the derivatives thereof to be incorporated into the vaccine composition of the present invention desirably ranges from 0.05 to 50 mg/0.2 ml and preferably 0.5 to 20 mg/0.2 ml.

The protective vaccine composition for dental caries of the present invention may further comprise an adjuvant such as alum, aluminum hydroxide, aluminum phosphate, aluminum sulfate and muramyl dipeptide; adjuvant fat-soluble components (agents for accelerating absorption) such as oleic acid, stearic acid and palmitic acid; humectants such as glycerin, sorbite, xylite, mannite, lactite, maltire and polyethylene glycols (such as PEG 400 and PEG 4,000); preservatives such as sorbic acid, chlorobutanol, benzoic acid, o-oxybenzoic acid ester, boric acid, dehydroacetic acid and thymol; and binders such as sodium polyacrylate, polyvinyl alcohol, polyvinyl pyrrolidone, sodium carboxy methyl cellulose, methyl cellulose, hydroxyethyl cellulose, carrageenan, sodium alginate, gum arabic, xanthane gum, montmorillonite, kaolin, hydrated silica, aluminum magnesium silicate and hectorite.

Alternatively, mammalian or birds are immunized with the protein antigen PAc of the present invention per se or a combination thereof with a surfactant and/or CTB to obtain antibodies and the resulting antibodies may be used in the protective vaccine composition for dental caries of the present invention as effective components.

According to the protective vaccine composition for dental caries, the antibody titer can effectively and simply be increased without pain by intranasally administering the protein antigen PAc.

In addition, the antibody titer of the vaccine composition of the present invention can more efficiently be increased if the protein antigen PAc is administered together with a surfactant, cholera toxin B or a bile acid or a derivative thereof.

Therefore, the present invention further includes two aspects, the one being a method for intranasally administering a vaccine composition for dental carries which comprises a protein antigen PAc and a carrier or a diluent and optionally a surfactant, cholera toxin B or a bile acid or a derivative thereof and the other being use of protein antigen PAc for the preparation of the vaccine composition for dental carries as nasal drops.

The present invention will hereunder be explained in more detail with reference to the following non-limitative Examples.

EXAMPLE 1

(1) Integration of the pac Gene into the Strain GS-5

The plasmid pPC77 carrying the pac gene of *Streptococcus mutans* NCTC 10449 and a shuttle vector pSA3 were cleaved with restriction enzymes Bam HI and Sph I respectively. The cleaved pPC77 and pSA3 were linked with a T4 DNA ligase, the resultant plasmid was inserted into host cells, *E. coli* strain HB 101 (deposited with National Institute for Genetics under the accession number of ME 8568) by a transformation technique and a clone which was resistant to chloramphenicol and sensitive to ampicillin and tetracycline was selected. Recombinant plasmids were extracted from clones whose capacity of producing PAc had been confirmed by a colony immune blot technique or Western blot technique, the size thereof was determined by agarose electrophoresis and it was thus found that all the clones had the recombinant plasmid of 16.4 kb. One of these plasmids was named K and the plasmid K was inserted into a strain, *S. mutans* GS-5, incapable of producing PAc by an electroporation technique to transform the strain. The resulting PAc-producing strain was named GS-5 (K-X).

In the foregoing operations, a plurality of strains, GS-5 (K-X) were obtained, but their PAc-producing abilities differed from each other. Among these strains, the strains, GS-5 (K-3) having excellent PAc-prducing ability and GS-5 (K-9) which produced PAc, but whose PAc-producing ability was inferior to that of the former were examined on the sites at which the pac gene was inserted.

(2) Determination of the Site at Which pac Gene Was Integrated

The strains GS-5 and GS-5 (K-3) were lysed with lysozyme and the plasmids were separated from the chromosomal DNA's. The resulting fractions containing plasmid were analyzed by agarose electrophoresis and it was found that any plasmids were not present in the fractions thus obtained from the strains GS-5 and GS-5 (K-3) as shown in FIG. 1. On the other hand, the same procedures were repeated using the strain GS-5 (K-9) and it was found that the intended plasmid was present in the fraction thus obtained from the strain GS-5 (K-9).

The chromosomal-DNA was cleaved with Eco RI and then the resultant products were analyzed by the conventional Southern blot technique. When Sam HI fragments of the gene resistant to erythromycin were used as a probe, the chromosomal DNA's of the strains GS-5 and GS-5 (K-9) did not show any reactivity, while the fragment of about 16 kb of the chromosomal DNA of the strains GS-5 (K-3) exhibited reactivity therewith.

The foregoing results clearly show that, in the strain GS-5 (K-3), the plasmid pSM1 was integrated into the chromosomal DNA of the strain GS-5 as a result of homologous recombination. On the other hand, in the strain GS-5 (K-9) which can produce PAc, but whose PAc-producing ability is inferior to that of the strain GS-5 (K-3), it is found that the pac gene was present in the plasmid, but not in the chromosomal DNA thereof.

The Southern blot analysis is detailed in the article of E. M. Southern (1975) entitled "Detection of Specific Sequences Among DNA Fragments Separated by Gel Electrophoresis", J. Mol. Biol., 98, pp. 503–517.

(3) Cultivation and Purification of rPAc (Recombinant PAc)

The *S. mutans* strain GS-5 (K-3) was cultured in an external solution obtained by dialyzing TTY broth or BHI broth, the resulting culture supernatant was salted out at a saturated concentration of ammonium sulfate (60%), the products salted out were dissolved in 50 mM Tris-HCl buffer, dialyzed against the same buffer and the resulting dialyzate (preparation) was passed through a DEAE-cellulose column which had been equilibrated with the same buffer in advance. After passing the bed volume of the same buffer through the column two times, elution was performed at a linear concentration gradient of NaCl ranging from 0 to 0.5 mole. As a result, PAc was eluted at an NaCl concentration of about 0.2 mole. This eluted fraction as such can be used as a purified preparation of rPAc. When the strain GS-5 (K-B) is used, the purification processes can be substantially simplified as described above since the content of rPAc in the culture supernatant is very high.

The rPAc thus prepared can be used as vaccines for dental caries in various forms.

In the same manner used above, an NCTC 10449 strain, a GS-5 strain and a GS-5 (K-9) strain were likewise cultured, PAc secreted in the culture supernatants was purified, and the amount thereof (expressed in the reduced amount of the proteins contained) was determined by the Lowry method. The results are listed in the following Table I as relative values. As seen from these results, the GS-5 (K-B) strain of the present invention produces PAc in high yield.

TABLE I

| Strain Used | Relative Amount of PAc Produced |
| --- | --- |
| *Streptococcus mutans* NCTC 10449 | 1 |
| *Streptococcus mutans* GS-5 | 0 |
| *Streptococcus mutans* GS-5 (K-3) | 48 |
| *Streptococcus mutans* GS-5 (K-9) | 12 |

(4) Immunization Test with rPAc

Compositions listed in the following Table II were dissolved in phosphate-buffered saline (PBS) and 0.1 ml each of the resulting solution was intraperitoneally injected twice in groups of mice (5 mice per group) at 10-days intervals to thus immunize the mice. 7 days after the second immunization, blood was sampled from the mice and the antibody titer against rPAc in blood was determined by the enzyme-linked immuno sorbent assay (ELISA method). The results obtained are summarized in Table II. In Table II, the antibody titer is expressed in the reciprocal of the highest rate of dilution at which the resulting serum showed reactivity in the ELISA method. In this respect, the serum was first diluted 10 times and thereafter it was diluted two times in order to determine the highest rate of dilution.

TABLE II

| Group No. | Amount of rPAc (in 1 ml) | Antibody Titer in Blood |
| --- | --- | --- |
| 1 | none (only PBS) | <10 |
| 2 | 100 μg | 980 |

EXAMPLE 2

Groups of 5-week-old BALB/c mice (each comprising 5 animals) were immunized by intranasally administering 10 μl each of a solution containing PAc alone or a mixed solution containing PAc as well as a surfactant, cholera toxin B or a bile acid (salt) (the composition thereof is given below), three times at one-week intervals and further 4 weeks after the third immunization a fourth immunization was likewise performed. Then blood was sampled from each mouse and the antibody titer in blood was determined by the ELISA method. The results obtained are listed in the following Table III. In Table III, the antibody titer is expressed in the titer of the serum diluted 100 times, which was obtained 7 weeks after the final intranasal immunization.

| Composition of the Mixed Solution (unit dose: 10 μl) | |
| --- | --- |
| Component | Amount |
| PAc (rPAc) | 1 mg/ml |
| Cholera toxin B | 0.5 mg/ml |
| Anionic surfactant | 0.2% by weight |
| Cationic surfactant | 0.2% by weight |
| Nonionic surfactant | 0.2% by weight |
| Bile acid (salt) | 0.2% by weight |

TABLE III

| Composition of the solution administered | ELISA $OD_{405}$ |
| --- | --- |
| PAc + cholera toxin B | 0.55 |
| PAc + benzethonium chloride | 0.52 |
| PAc + SDS[*1] | 0.42 |
| PAc + Triton X-100[*2] | 0.25 |
| PAc + glycolic acid | 0.50 |
| PAc + sodium glycolate | 0.52 |
| PAc alone | 0.12 |

[*1]SDS: sodium lauryl sulfate.
[*2]Triton X-100: polyoxyethylene alkyl phenyl ether.

EXAMPLE 3

The following exemplary preparations 1 to 13 of the protective vaccine composition for dental caries according to the present invention were prepared.

| Preparation 1 | |
| --- | --- |
| Benzethonium chloride | 0.1 g |
| Glycerin | 0.8 g |
| Hydroxyethyl cellulose | 0.8 g |
| PAc | 0.25 g |
| Purified water | balance |
| total | 100 g |
| Preparation 2 | |
| Sodium lauryl sulfate | 0.4 g |
| Xylite | 0.5 g |
| Hydroxymethyl cellulose | 0.8 g |
| PAc | 0.25 g |
| Benzoic acid | 0.1 g |
| Purified water | balance |
| total | 100 g |
| Preparation 3 | |
| Sucrose monopalmitic acid ester | 1.2 g |
| sorbite | 0.6 g |
| Methyl cellulose | 0.6 g |
| PAc | 0.4 g |
| Purified water | balance |
| total | 100 g |
| Preparation 4 | |
| Glycerin | 0.8 g |
| Hydroxyethyl cellulose | 0.5 g |
| rPAc | 0.25 g |
| Cholera toxin B | 0.08 g |
| Butyl Paraben HCl | 0.1 g |
| Purified water | balance |
| total | 100 g |
| Preparation 5 | |
| Benzethonium chloride | 0.1 g |
| Polyoxyethylene hardened castor oil | 0.8 g |
| Xylite | 0.5 g |
| Hydroxymethyl cellulose | 0.8 g |
| rPAc | 0.5 g |
| Benzoic acid | 0.1 g |
| Alum | 0.02 g |
| Purified water | balance |
| total | 100 g |
| Preparation 6 | |
| Cetyl pyridinium chloride | 1.5 g |
| Sorbite | 0.7 g |
| Gum arabic | 0.3 g |
| rPAc | 0.5 g |
| Muramyl dipeptide | 0.05 g |
| Purified water | balance |
| total | 100 g |
| Preparation 7 | |
| Glycerin monolauric acid ester | 0.4 g |
| Polyoxyethylene sorbitan fatty acid ester | 0.5 g |
| Glycerin | 0.8 g |
| Hydroxymethyl cellulose | 0.5 g |
| PAc | 0.25 g |
| Cholera toxin B | 0.08 g |
| Purified water | balance |
| total | 100 g |
| Preparation 8 | |
| Glycerin | 0.8 g |
| Hydroxyethyl cellulose | 0.5 g |
| PAc | 0.8 g |
| Butyl Paraben HCl | 0.1 g |
| Stearic acid | 0.05 g |
| Purified water | balance |

-continued

| | |
|---|---|
| total | 100 g |
| Preparation 9 | |
| Polyoxyethylene sorbitan stearic acid ester | 0.5 g |
| Glycerin | 0.8 g |
| Hydroxyethyl cellulose | 0.5 g |
| PAc | 0.5 g |
| Cholera toxin B | 0.08 g |
| Lauryl di(aminoethyl)glycine hydrochloride | 0.2 g |
| Purified water | balance |
| total | 100 g |
| Preparation 10 | |
| Chlorohexyzine gluconate | 0.1 g |
| Sodium polyacrylate | 0.2 g |
| rPAc | 0.25 g |
| Aluminum hydroxide | 0.1 g |
| Oleic acid | 0.5 g |
| Triton 100 | 0.8 g |
| Purified water | balance |
| total | 100 g |
| Preparation 11 | |
| Glycerin | 0.8 g |
| PAc | 0.08 g |
| Butyl Paraben hydrochloride | 0.1 g |
| Sodium glycocholate | 0.1 g |
| Stearic acid | 0.05 g |
| Alum | 0.1 g |
| Purified water | balance |
| total | 100 g |
| Preparation 12 | |
| Sorbite | 2.0 g |
| rPAc | 0.05 g |
| Butyl Paraben hydrochloride | 0.1 g |
| Cholic acid | 0.2 g |

-continued

| | |
|---|---|
| Polyoxyethylene sorbitan fatty acid ether | 1.0 g |
| Purified water | balance |
| total | 100 g |
| Preparation 13 | |
| Glycerin | 2.0 g |
| rPAc | 0.08 g |
| Sodium glycocholate | 0.1 g |
| Cholera toxin B | 0.04 g |
| Purified water | balance |
| total | 100 g |

What is claimed is:

1. A method for preparing a vaccine against dental caries comprising integrating a protein antigen-expressing gene (Pac-expressing gene) into a *Streptococcus mutans* GS-5 strain to produce a variant bacterial strain; culturing the variant bacterial strain; the variant *Streptococcus mutans* GS-5 strain encoding a protein antigen to produce the protein antigen on the surface of cells of *Streptococcus mutans* or to extracellularly produce the protein antigen, wherein the protein antigen produced has a molecular weight ranging from about 170,000 to 220,000; and recovering the protein antigen produced by the variant bacterial strain.

2. The method of claim 1 wherein the protein antigen has a molecular weight of about 190,000.

3. The method of claim 1 wherein the *Streptococcus mutans* GS-5 strain is GERM BP-2436.

4. The method of claim 1 wherein a *Streptococcus mutans* GS-5 (K-3) strain, FERM BP-2437, is cultured.

* * * * *